(12) United States Patent
Simpson

(10) Patent No.: US 6,926,407 B2
(45) Date of Patent: Aug. 9, 2005

(54) APPARATUS AND METHOD FOR MEASURING A HUE OF A PREDETERMINED PRIMARY COLOR IN REFLECTED LIGHT

(76) Inventor: Trefford Simpson, 411 Laurel Gate Drive, Waterloo, Ontario (CA), N2T 2S6

(*) Notice: Subject to any disclaimer, the term of this patent is extended or adjusted under 35 U.S.C. 154(b) by 434 days.

(21) Appl. No.: 10/183,173

(22) Filed: Jun. 28, 2002

(65) Prior Publication Data

US 2004/0001203 A1 Jan. 1, 2004

(51) Int. Cl.[7] .................... A61B 3/10; G01N 21/25; G01N 21/27
(52) U.S. Cl. ............... 351/205; 356/243.5; 356/402; 356/940; 356/943
(58) Field of Search ................. 351/205, 221; 356/402–425, 243.4, 243.5, 928, 931, 939, 940, 943; 600/558

(56) References Cited

U.S. PATENT DOCUMENTS

| | | | | |
|---|---|---|---|---|
| 4,330,062 A | * | 5/1982 | Conway et al. | 356/407 |
| 4,464,054 A | * | 8/1984 | Karras et al. | 356/406 |
| 4,838,679 A | | 6/1989 | Bille | |
| 4,900,145 A | | 2/1990 | Akiyama | |
| 5,119,814 A | | 6/1992 | Minnich | |
| 5,141,303 A | | 8/1992 | Yamamoto et al. | |
| 5,168,320 A | * | 12/1992 | Lutz et al. | 356/402 |
| 5,240,006 A | | 8/1993 | Fujii et al. | |
| 5,835,189 A | | 11/1998 | Quigley et al. | |
| 5,905,562 A | * | 5/1999 | Isogai et al. | 351/205 |
| 6,144,004 A | * | 11/2000 | Doak | 356/425 |
| 6,157,445 A | * | 12/2000 | Macfarlane et al. | 356/243.5 |
| 6,157,453 A | * | 12/2000 | Tamanti et al. | 356/425 |
| 6,239,867 B1 | * | 5/2001 | Aggarwal | 356/425 |
| 6,247,812 B1 | | 6/2001 | Miehle et al. | |
| 6,750,970 B2 | * | 6/2004 | Masuda | 356/425 |
| 2001/0007474 A1 | | 7/2001 | Takada | |
| 2001/0016695 A1 | | 8/2001 | Mahashi et al. | |
| 2001/0024263 A1 | | 9/2001 | Nanjyo | |
| 2001/0024266 A1 | | 9/2001 | Apple et al. | |
| 2001/0028438 A1 | | 10/2001 | Matsumoto | |
| 2001/0028439 A1 | | 10/2001 | Itoh | |
| 2001/0028441 A1 | | 10/2001 | Okamoto et al. | |
| 2001/0033364 A1 | | 10/2001 | Cabib et al. | |
| 2001/0038439 A1 | | 11/2001 | Doherty | |
| 2002/0003606 A1 | | 1/2002 | Pettit | |
| 2002/0003607 A1 | | 1/2002 | Toida | |
| 2002/0005934 A1 | | 1/2002 | Walther et al. | |
| 2003/0128362 A1 | * | 7/2003 | Gudaitis et al. | 356/405 |

OTHER PUBLICATIONS

"Automated Measurement of Bulbar Redness", by P. Fieguth and T. Simpson, Investigative Ophthalmology and Vision Science, Feb., 2002, vol. 43, Part 2, pp. 340–347.

* cited by examiner

Primary Examiner—Brian L. Casler
Assistant Examiner—John R. Sanders

(57) ABSTRACT

The invention provides an apparatus for measuring a hue of a predetermined primary color included in light reflected from a surface. The apparatus has a diffuse light source for creating incident light comprising a plurality of primary colors including the predetermined primary color, the incident light being directed onto the surface. The incident light is reflected from the surface to produce the reflected light. The apparatus also has a photometer for receiving and analyzing the reflected light to provide objective chromaticity data representing the hue of the predetermined primary color, and a scale adapted for converting the objective chromaticity data to a clinical score measuring the hue of the predetermined primary color in the reflected light.

9 Claims, 5 Drawing Sheets

APPARATUS AND METHOD FOR MEASURING A HUE OF A PREDETERMINED PRIMARY COLOR IN REFLECTED LIGHT

FIELD OF THE INVENTION

This invention relates to devices for measuring a hue of a primary color included in light, and more particularly, an apparatus for measuring a hue of a predetermined primary color included in light reflected from a surface.

BACKGROUND OF THE INVENTION

In clinical practice, evaluation of the extent to which a patient's eyeball, or bulbus oculi, is red or some other color is often indicative of a condition of the bulbus oculi. Although red is generally the most relevant color, colors other than red can be relevant. Also, the extent of "redness" of an exposed portion of a tarsal area, i.e., the part of the eyelid which is normally in contact with the eyeball, is often indicative of a condition of the eyeball or the patient. A clinician is often concerned with determining the extent of redness of the bulbus oculi or the tarsal area, although redness is only one possible indicator. The term clinician, as used herein, means an optometrist, an ophthalmologist, or a general medical practitioner.

In particular, the clinician typically assesses the redness of an exposed portion of the bulbus oculi or an exposed portion of the tarsal area, as the case may be, over a period of time, during treatment of the patient's condition. Detecting variations (i.e., decrease or increase) in redness of the bulbus oculi or the tarsal area during treatment can be helpful in assessing changes in a patient's condition. For example, a gradual increase in redness of the bulbus oculi (or the tarsal area), or no change in redness, may suggest to the clinician that changes in treatment are warranted.

In certain circumstances, the clinician may wish to compare different responses to treatment of similar conditions in a number of patients. As in the case of assessment of a single patient during treatment, a reliably consistent measurement of redness of the bulbus oculi or the tarsal area would assist the clinician in assessing the responses to treatment.

Known methods and devices for assessing the redness of an exposed portion of the bulbus oculi or an exposed portion of the tarsal area have not provided consistent measurements of redness. In general, redness is determined by the clinician visually comparing the redness of the exposed portion of the bulbus oculi or tarsal area, as the case may be, to reference color images. As indicated, colors other than red may be of interest, and in those circumstances, the reference color images would be of the color of interest. Typically, the reference color images are photographic representations of eyes with varying hues of red. Alternatively, the reference color images can be verbal (written) descriptions of various hues of red. The clinician is to apply the reference color images by visually comparing the redness of the exposed portion of the photographic or written reference color images, as the case may be. This method of determining redness is very approximate and unreliable. Because white light comprises an equal mixture of the primary colors, i.e., red, green, and blue, this known practice is, in effect, a crude estimate of the extent to which a particular primary color is reflected by the exposed portion being examined.

Other ways of assessing redness have been proposed, to provide more consistent assessment. For example, in P. Fieguth and T. Simpson, "Automated Measurement of Bulbar Redness", Investigative Ophthalmology and Vision Science, February 2002, Vol. 43, Part 2, pages 340–7, a method of evaluating redness is disclosed in which an image of an exposed portion of the bulbus oculi of a subject was analyzed using numeric processing of pixels in the image by a computer to determine the extent of redness. The process was repeated with various subjects. The images were derived from photographs, however, with the result that some loss or distortion of relevant color information, when the image is captured and prepared for the numeric processing, is possible.

As noted, although the extent of redness is of interest, other colors may also be of interest to the clinician. Various other devices and methods are known for evaluating a particular condition of the bulbus oculi. However, these known devices and methods are not directed to measurement of the extent of redness (or any other color) of an exposed portion of the bulbus oculi or the tarsal area, as the case may be. For example, in U.S. Pat. No. 4,900,145 (Akiyama), an apparatus is disclosed which includes a laser beam projector. A laser beam sent from the projector scans a region inside the patient's bulbus oculi, to provide data for an evaluation of the concentration of protein in the anterior chamber of the eye. The invention disclosed in Akiyama is not directed to determining the color of the surface of an exposed portion of the bulbus oculi.

There is therefore a need for an apparatus and a method for measuring a hue of a predetermined primary color in light reflected from a surface.

SUMMARY OF THE INVENTION

In a broad aspect of the present invention, there is provided an apparatus for measuring the hue of a predetermined primary color included in light reflected from a surface. The apparatus has a diffuse light source for creating incident light comprising a plurality of primary colors including the predetermined primary color, the incident light being directed onto the surface. The incident light is reflected from the surface to produce the reflected light. The apparatus also has a photometer for receiving and analyzing the reflected light to provide objective chromaticity data representing the hue of the predetermined primary color, and a scale adapted for converting the objective chromaticity data to a clinical score measuring the hue of the predetermined primary color in the reflected light. When the incident light is directed onto the surface, reflected light is received and analyzed by the photometer to provide the objective chromaticity data, and the scale converts the objective chromaticity data to the clinical score to measure the hue of the predetermined color in the reflected light.

In another aspect of the invention, there is provided an apparatus for measuring a hue of a predetermined primary color included in a beam of light reflected from a surface of a part of a patient's body. The apparatus has a diffuse light source for creating a beam of incident light comprising a plurality of primary colors including the predetermined primary color. The beam of incident light is directed onto the surface of the body part. In addition, the beam of incident light is substantially coaxial with an incident light beam axis. The beam of incident light is reflected from the surface of the body part to produce the beam of reflected light, and the beam of reflected light is substantially coaxial with a reflected light beam axis. The apparatus also has a support and a target, both of which are for positioning the surface. The support is for positioning the surface relative to the light source and the photometer so that the reflected light is received in the photometer. The target is for viewing by the patient for positioning the surface relative to the light source and the photometer so that the reflected light is received in the photometer. In addition, the apparatus has a photometer for receiving and analyzing reflected light to provide objective chromaticity data representing the hue of the predetermined primary color. The incident light beam axis and the reflected light beam axis form a predetermined angle between 30° and 50° so that the reflected light is received in the photometer. The apparatus also has a scale adapted for converting the objective chromaticity data to a clinical score measuring the hue of the predetermined primary color in the reflected light. When the incident light is directed onto the surface and the incident light beam axis and the reflected light beam axis form the predetermined angle, reflected light is received and analyzed by the photometer to provide the objective chromaticity data, and the scale converts the objective chromaticity data to the clinical score to measure the hue of the predetermined color in the reflected light.

According to yet another aspect of the present invention, the invention provides a method of measuring a hue of a predetermined primary color included in light reflected from a surface. The method comprises the steps of, first, providing a diffuse light source for creating incident light comprising a plurality of primary colors including the predetermined primary color, the incident light being directed onto the surface, the incident light reflecting from the surface to produce the reflected light, and second, providing a photometer for receiving and analyzing the reflected light to provide objective chromaticity data representing the hue of the predetermined primary color. The method also includes the steps of positioning the surface relative to the light source and the photometer so that the reflected light is received in the photometer, and providing a scale adapted for converting the objective chromaticity data to a clinical score measuring the hue of the predetermined primary color in the reflected light.

According to yet another aspect, the invention provides a method of assessing a condition of a bulbus oculi by measuring a hue of a predetermined primary color included in light reflected from a surface of an exposed portion of the bulbus oculi. The method comprises the steps of, first, providing a diffuse light source for creating incident light comprising a plurality of primary colors including the predetermined primary color directed onto the exposed portion of the bulbus oculi, the incident light being reflected from the exposed portion of the bulbus oculi to produce the reflected light, and, second, providing a photometer for receiving and analyzing the reflected light to provide objective chromaticity data representing the hue of the predetermined primary color. The method also includes the steps of providing a scale adapted for converting the objective chromaticity data to a clinical score measuring the hue of the predetermined primary color in the reflected light, and comparing the clinical score to a control clinical core measuring a control hue of the predetermined primary color related to a predetermined health condition of the bulbus oculi, whereby the condition of the bulbus oculi is assessed.

According to yet another aspect, the invention provides a method of assessing a condition of a tarsal area by measuring a hue of a predetermined primary color included in light reflected from a surface of an exposed portion of the tarsal area. The method comprises the steps of providing a diffuse light source for creating incident light comprising a plurality of primary colors including the predetermined primary color directed onto the exposed portion of the tarsal area, the incident light being reflected from the exposed portion of the tarsal area to produce the reflected light, and providing a photometer for receiving and analyzing the reflected light to provide objective chromaticity data representing the hue of the predetermined primary color. The method also includes the steps of providing a scale adapted for converting the objective chromaticity data to a clinical score measuring the hue of the predetermined primary color in the reflected light, and comparing the clinical score to a control clinical score measuring a control hue of the predetermined primary color related to a predetermined health condition of the tarsal area, whereby the condition of the tarsal area is assessed.

BRIEF DESCRIPTION OF THE DRAWINGS

The invention will be better understood with reference to the drawings, in which.

BRIEF DESCRIPTION OF THE PREFERRED EMBODIMENT(S)

Figure 1:
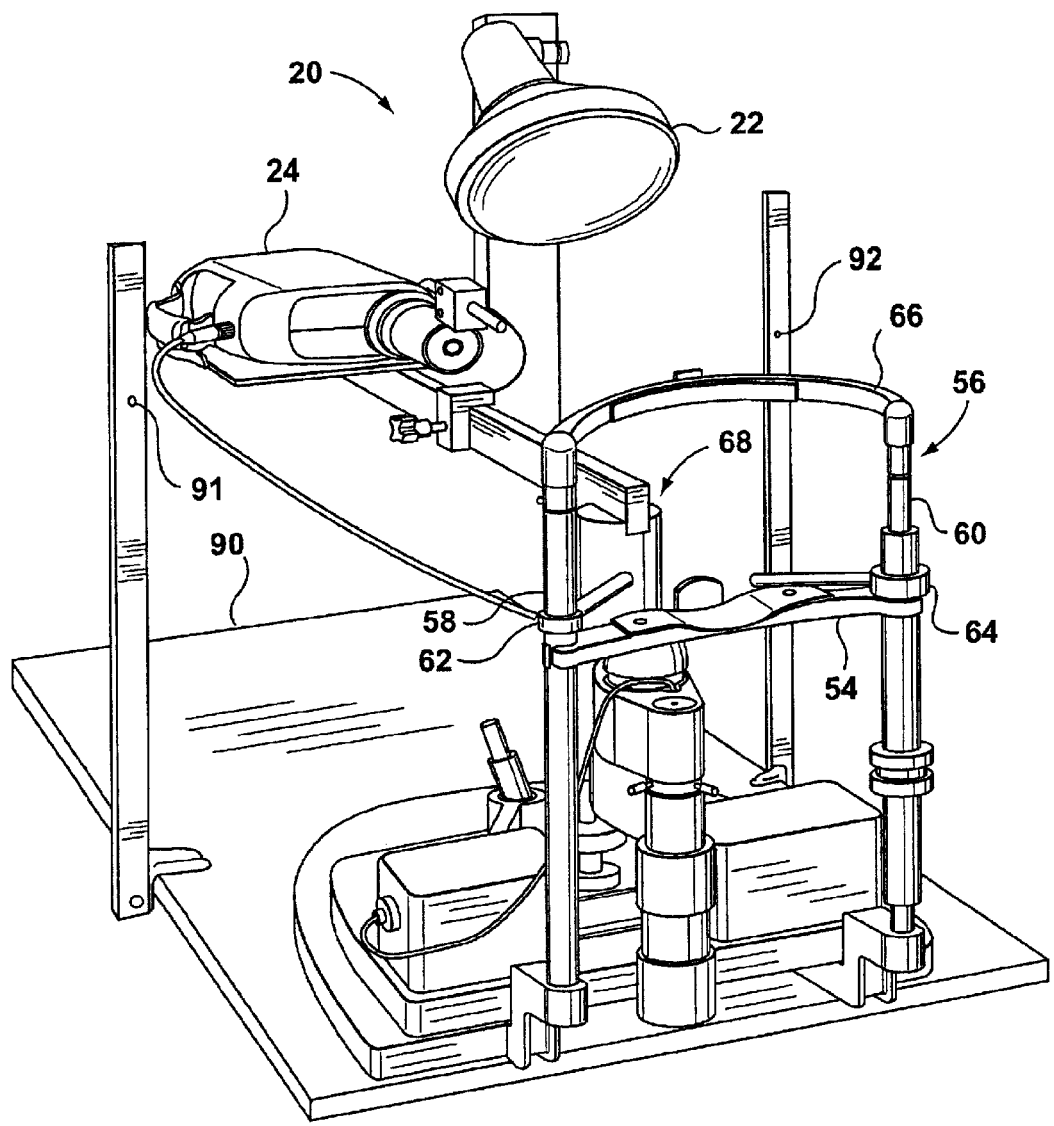
FIG. 1 is an isometric view of a preferred embodiment of the apparatus.
Figure 2:
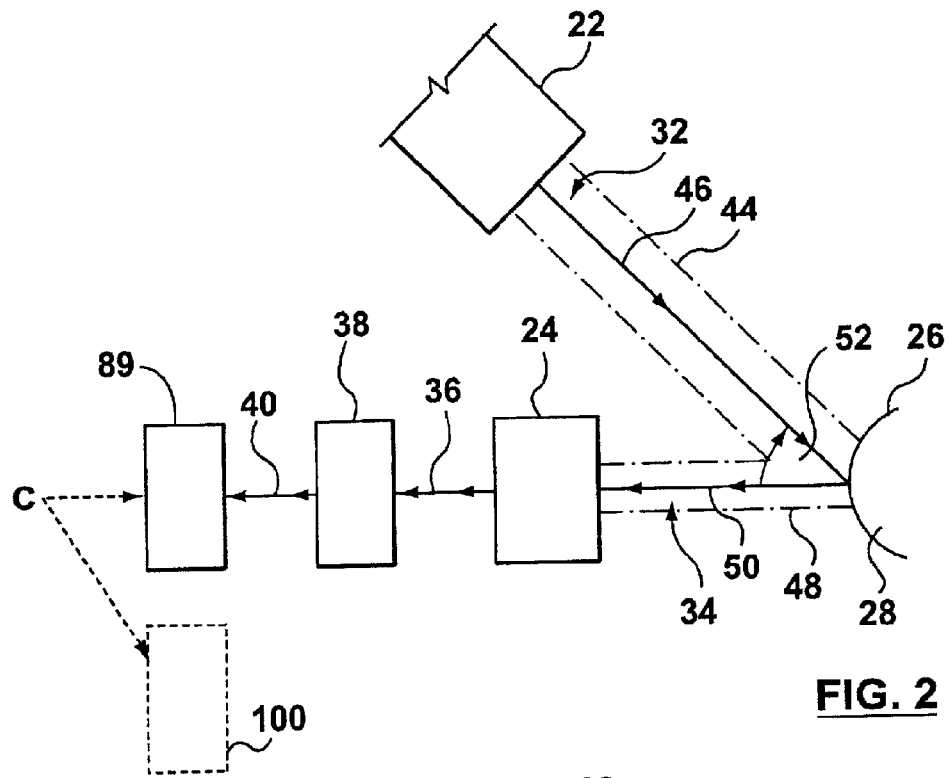
FIG. 2 is a schematic drawing representing light from a light source reflected from an exposed portion of a bulbus oculi to a photometer.

Reference is first made to FIGS. 1 and 2 to describe a preferred embodiment of an apparatus indicated generally by the numeral 20 in accordance with the invention. FIG. 1 shows that the apparatus 20 includes a diffuse light source 22 and a photometer 24. As represented in FIG. 2, when a surface of a part of a patient's body comprising a surface 26 of an exposed portion of a bulbus oculi 28 of a patient (not shown) is in the apparatus 20, incident light 32 from the light source 22 is directed at the surface 26 of an exposed portion of the bulbus oculi 28 to produce reflected light 34.

The incident light 32, created by the diffuse light source 22, is white light. As is known in the art, the incident light 32 comprises a plurality of primary colors and specifically, an equal mixture of red, blue and green light. The plurality of primary colors includes a predetermined primary color (not shown). Because the incident light comprises a plurality of primary colors, reflected light 34 also comprises a plurality of primary colors, however, the mixture of the primary colors in the reflected light 34 is affected by the colors on the surface 26. In particular, and as is known in the art, the reflected light 34 comprises the primary colors to the extent that they are reflected by the surface 26, and not absorbed by the surface 26. Accordingly, as is known in the art, the extent to which the mixture of the primary colors comprising reflected light 34 includes the predetermined primary color depends on the extent to which the predetermined primary color is reflected by the surface 26. The photometer 24 is adapted to receive and analyze reflected light 34 to provide objective chromaticity data 36, as is known in the art. Typically, the objective chromaticity data 36 is provided as chromaticity coordinates meeting specifications established by the Commission Internationale de L'Eclairage (the International Committee on Illumination), Kegelgasse 27 A-1030, Wien, Austria, for example, as set out in Colorimetry (2d ed.) 1986, Publication CIE 15.2 (ISBN 3 900 734

00 3). The objective chromaticity data 36 represents the hue of the predetermined primary color in the reflected light. As shown in FIG. 2, the apparatus 20 also includes a scale 38 adapted for converting the objective chromaticity data 36 to a clinical score 40 measuring the hue of the predetermined primary color in the reflected light 34. Preferably, the scale 38 is developed by empirically comparing subjectively determined hues (for example, subjectively determined redness) and objective chromaticity data.

In the preferred embodiment, as can be seen in FIG. 2, the diffuse light source 22 creates a beam of incident white light 44 which is directed onto the surface 26 of an exposed portion of the bulbus oculi 28. The beam of incident light 44 is substantially coaxial with an incident light beam axis 46. As also shown schematically in FIG. 2, the beam of incident light 44 is reflected from the surface 26 of an exposed portion of the bulbus oculi 28 to produce a beam of reflected light 48. The beam of reflected light 48 is substantially coaxial with a reflected light beam axis 50. The incident light beam axis 46 and the reflected light beam axis 50 form a predetermined angle 52 so that the beam of reflected light 48 is received in the photometer 24. Preferably, the predetermined angle 52 is between approximately 30° and approximately 50°. Also, in the preferred embodiment, the predetermined angle 52 is approximately 45°.

Figure 4:
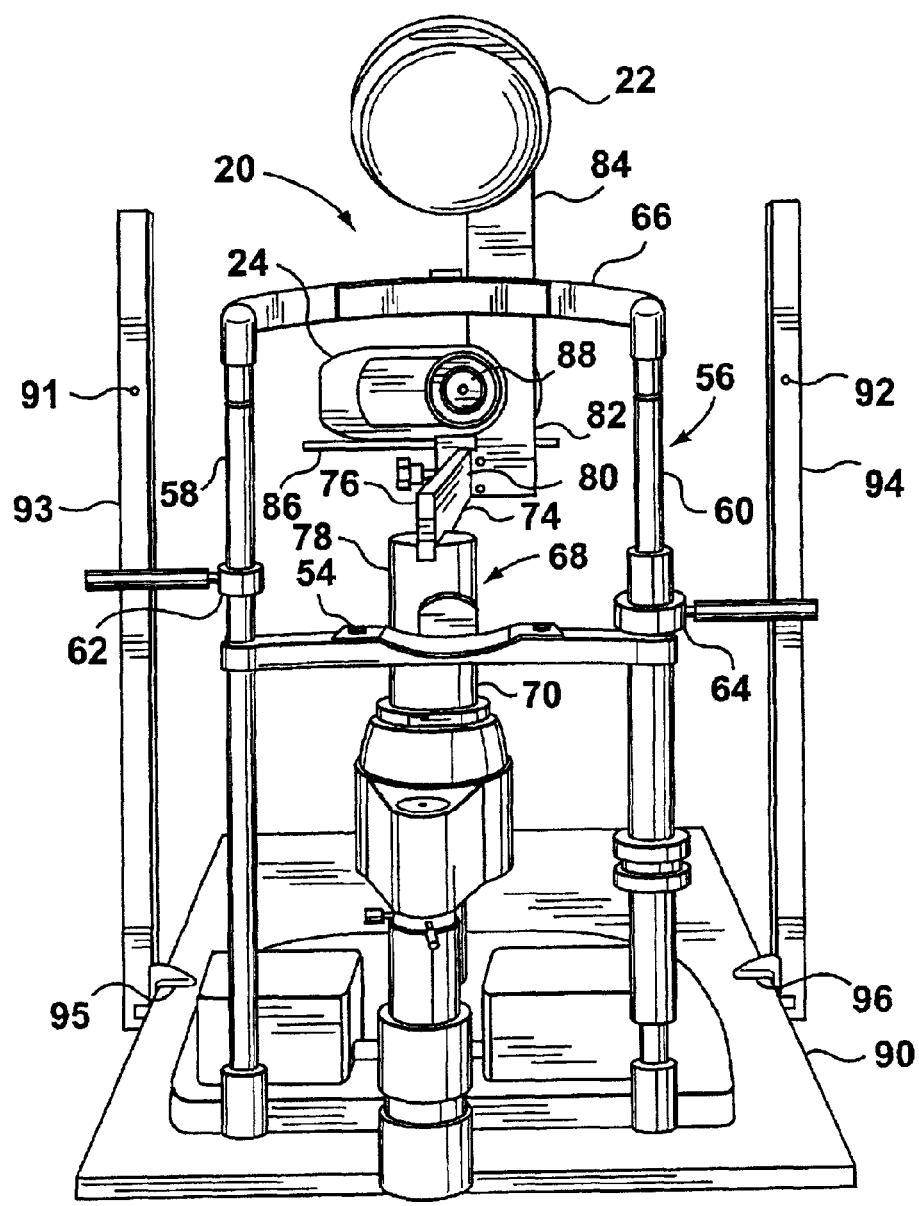
FIG. 4 is a front view of the apparatus of FIG. 1.

It is also preferred that the apparatus 20 includes a movable chin support 54, as can be seen in FIGS. 1 and 4. Preferably, the movable chin support 54 is mounted in a frame 56 comprising a pair of upright support members 58, 60 including height adjustment means 62, 64 for adjusting the height at which the chin support 54 is positioned, as is known in the art. As can be best seen in FIG. 4, the frame 56 preferably also includes a transverse member 66 to add strength to the frame 56. The support 54 is for positioning the surface 26 of an exposed portion of the bulbus oculi 28 relative to the light source 22 and the photometer 24 so that the reflected light 34 is received in the photometer 24 for analysis.

Preferably, the light source 22 is supported and positioned by a support assembly 68, as shown in FIGS. 1 and 4. While various other arrangements could be employed, in the construction shown in FIGS. 4 and 5, the support assembly 68 comprises a main substantially vertical support member 70 supporting a cross member 74 extending substantially horizontally from the main support member 70. A proximal end 76 of the cross member 74 is attached to the main support member 70 at a top portion 78 of the main support member 70, and a distal end 80 of the cross member 74 is attached to a light support member 82 which extends substantially vertically from the distal end 80 of the cross member 74. Preferably, the light source 22 is supported and positioned by the light support member 82 at a top end 84 of the light support member 82.

Figure 5:
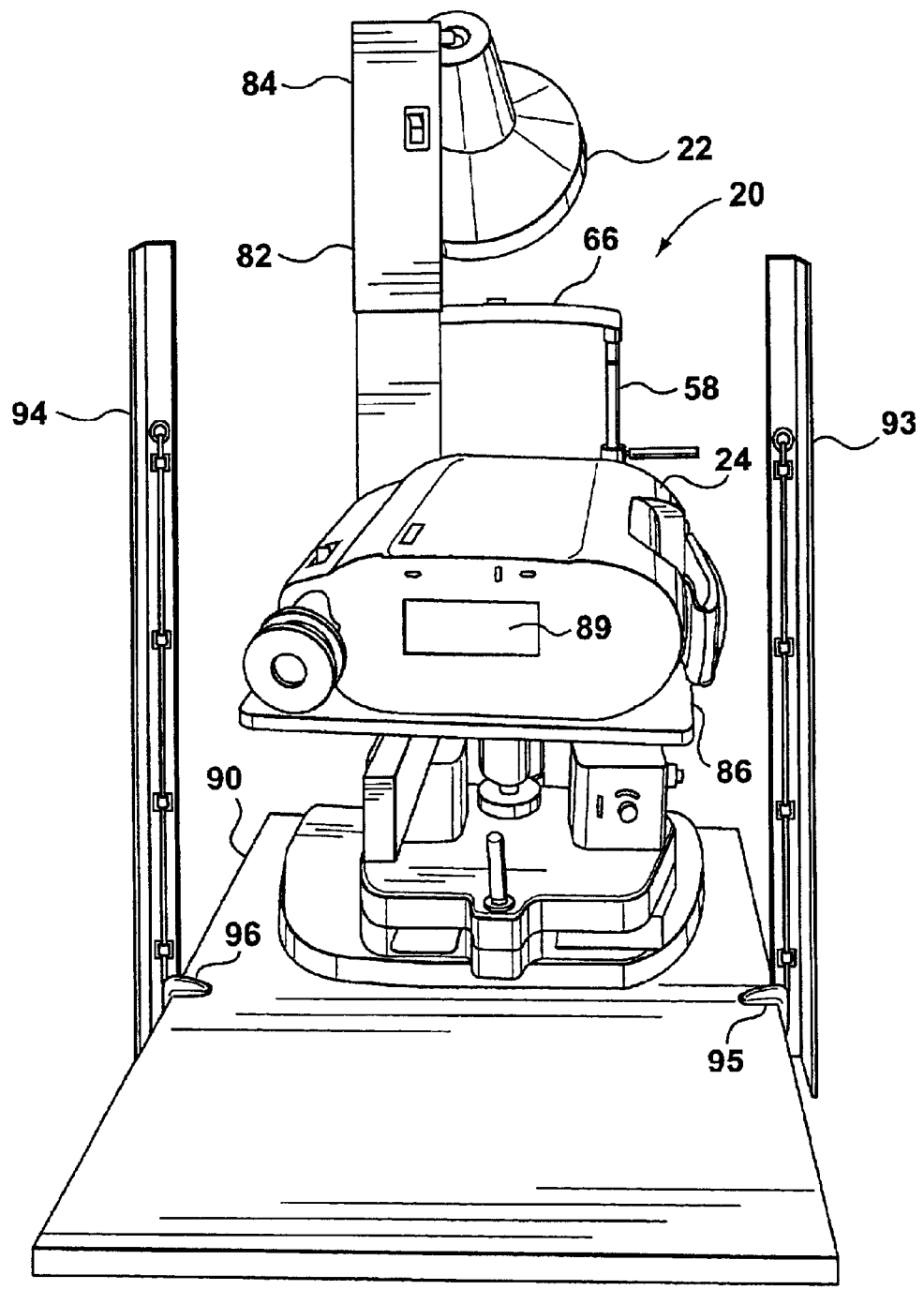
FIG. 5 is a back view of the apparatus of FIG. 1.

Various arrangements can be employed to support the photometer 24. However, as shown in FIGS. 1, 4 and 5, it is preferred that the photometer 24 be positioned on a photometer platform 86 such that a light-receiving lens 88 of the photometer 24 is positioned below, and substantially vertically aligned with, the light source 22. Preferably, and as known in the art, the photometer 24 also includes a display portion 89 (as shown in FIG. 5) for displaying the objective chromaticity data 36. Preferably, the photometer platform 86 is attached at or adjacent to the distal end 80 of the cross member 74. Although various forms of bases can be employed to support the apparatus 20, it is preferred that the apparatus 20 is positioned on a table top 90 or other suitable work surface, being a substantially horizontal and stable surface, as is known in the art.

It is also preferred that the apparatus 20 includes targets 91, 92, as shown in FIGS. 1 and 4, for viewing by the patient to position the surface 26 of an exposed portion of the bulbus oculi 28 relative to the light source 22 and the photometer 24 so that the reflected light 34 is received in the photometer 24. It is preferred that the targets 91, 92 are small electric lights positioned at a convenient height on target supports 93, 94. Preferably, the target supports 93, 94 are attached to the table top 90 using clamps 95, 96 or any suitable attachment device, as is known in the art.

Figure 6:
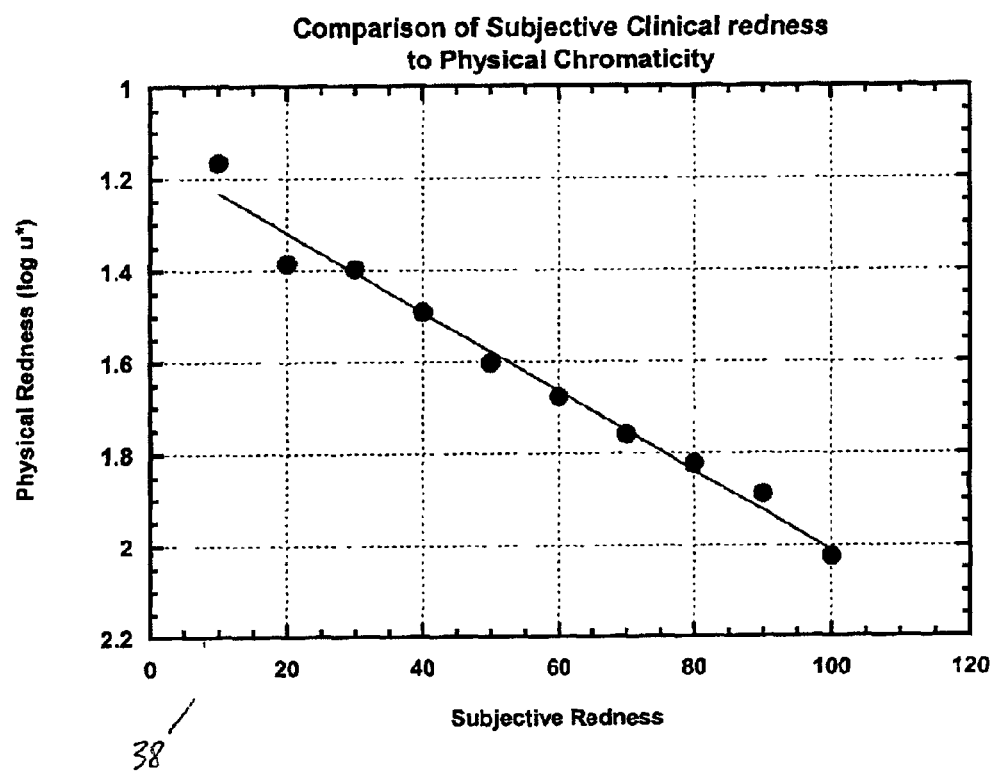
FIG. 6 is a comparison of subjectively evaluated redness and chromaticity.

In use, when the patient is to be examined, the patient's chin (not shown) is placed on the chin support 54. When incident light 32 comprising a plurality of primary colors including a predetermined primary color is directed onto the surface 26 of an exposed portion of the bulbus oculi 28, reflected light 34 is produced and reflected to the photometer 24. The reflected light 34 also comprises a plurality of primary colors, including the predetermined primary color, and is received and analyzed by the photometer 24 to provide the objective chromaticity data 36. The scale 38 converts the objective chromaticity data 36 to the clinical score 40 to measure the hue of the predetermined color in the reflected light 34. In this way, a clinician (schematically represented by C in FIG. 2) is able to assess readily and consistently the patient's condition as indicated by the patient's bulbus oculi 28. The scale 38 can be presented as a graph (as shown in FIG. 6) or a feature included in the photometer which results in the clinical score being displayed on the display portion 89, as represented in FIG. 2.

If the patient had previously been examined using the apparatus 20, then, for convenience, the positioning of the chin support 54, the light source 22, and the photometer 24 would preferably be similar to the positioning of those respective elements used in previous examinations. Similarity in positions of these various elements of the apparatus 20 would result in the angle 52 formed between the incident light beam axis 46 and the reflected light beam axis 50 being similar to the corresponding angles formed in previous examinations of the patient. This would tend to result in greater consistency in measurements for the patient in question.

Also, it is preferred that one of the targets 91, 92 would also be used to position the surface 26 of the exposed portion of the bulbus oculi 28 relative to the light source 22 and the photometer 24. The use of the targets 91, 92 in this way also tends to result in greater consistency between examinations.

As previously described, although the predetermined primary color can be red, blue, or green, in the majority of cases, the predetermined primary color is red because red is most often the color which is indicative of a particular condition.

Figure 3:
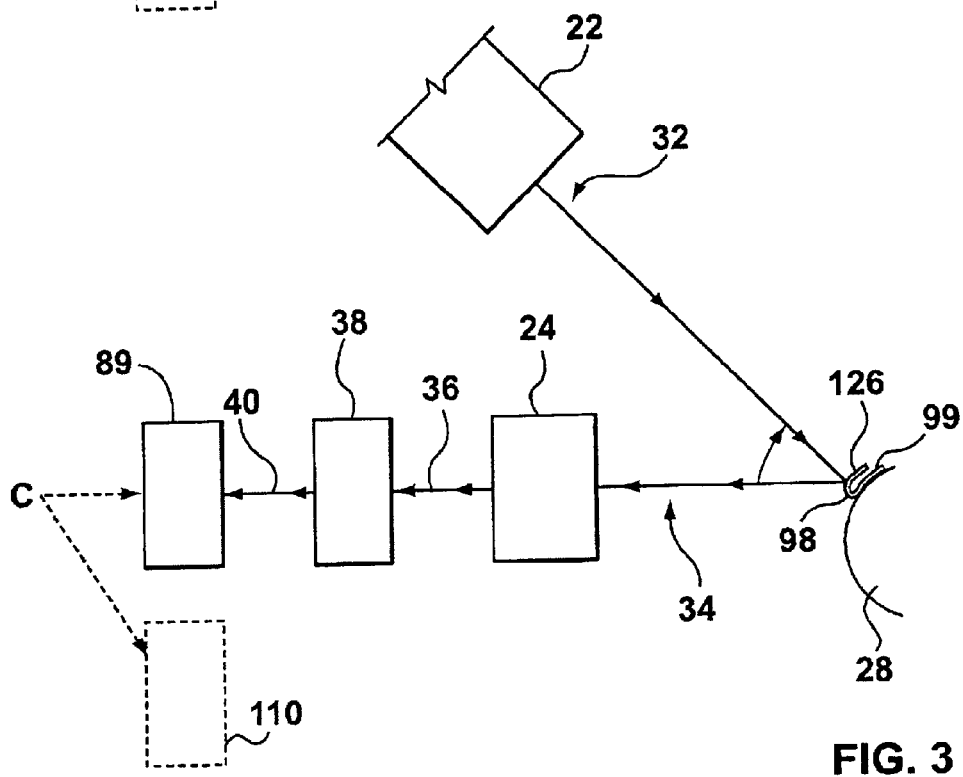
FIG. 3 is a schematic drawing representing light from a light source reflected from an exposed portion of a tarsal area to a photometer.

As shown in FIG. 3, a surface 126 of a part of a patient's body can, in the alternative, comprise a surface of an exposed portion of a tarsal area 98. As is known in the art, the exposed portion of the tarsal area 98 becomes exposed when the patient's eyelid 99 is turned back on itself. The redness of the tarsal area 98 is known to be indicative of certain conditions. As shown schematically in FIG. 3, the apparatus 20 can be used by a clinician (schematically represented by C in FIG. 3) to measure the hue of a predetermined primary color, such as red, included in reflected light 34 directed into the photometer 24 from the surface 126 of the exposed portion of the tarsal area 98. Also, as shown in FIG. 3, the photometer 24 receives and analyzes the reflected light 34 to produce objective chromaticity data 36, and the scale 38 converts the objective chromaticity data 36 to the clinical score 40.

The apparatus 20 can be used in a method for assessing a condition of the bulbus oculi 28 by measuring a hue of a predetermined primary color included in light 34 reflected from the surface 26 of the exposed portion of the bulbus oculi 28. Preferably, the method comprises, first, the step of providing the diffuse white light source 22 for creating incident light 32 comprising a plurality of primary colors including the predetermined primary color directed onto the exposed portion of the bulbus oculi 28. The incident light 32 is reflected from the surface 26 of the exposed portion of the bulbus oculi 28 to produce the reflected light 34.

The second step in the method is to provide the photometer 24 for receiving and analyzing the reflected light 34 to provide objective chromaticity data 36 representing the hue of the predetermined primary color. Next, the scale 38 is provided which is adapted for converting the objective chromaticity data 36 to the clinical score 40 measuring the hue of the predetermined primary color in the reflected light 34. Finally, and as represented schematically in FIG. 2, the clinical score 40 is compared by the clinician (represented by C in FIG. 2) to a control clinical score 100 which measures a control hue (not shown) of the predetermined primary color related to a predetermined health condition of the bulbus oculi 28, so that the condition of the bulbus oculi 28 is thereby assessed.

In a similar manner, the apparatus 20 can also be used in a method to assess a condition of the tarsal area 98 by measuring a hue of a predetermined primary color included in light 34 reflected from the surface 126 of the exposed portion of the tarsal area 98. Preferably, the method comprises, first, the step of providing the diffuse white light source 22 for creating incident light 32 comprising a plurality of primary colors including the predetermined primary color directed onto the exposed portion of the tarsal area 98. The incident light 32 is reflected from the surface 126 of the exposed portion of the tarsal area 98 to produce the reflected light 34.

The second step in the method is to provide the photometer 24 for receiving and analyzing the reflected light 34 to provide objective chromaticity data 36 representing the hue of the predetermined primary color. Next, the scale 38 is provided which is adapted for converting the objective chromaticity data 36 to the clinical score 40 measuring the hue of the predetermined primary color and the reflected light 34. Finally, and as represented schematically in FIG. 3, the clinical score 40 is compared by the clinician (represented by C in FIG. 3) to a control clinical score 110 which measures a control hue (not shown) of the predetermined primary color related to a predetermined health condition of the tarsal area 98, so that the condition of the tarsal area 98 is thereby assessed.

It will be evident to those skilled in the art that the invention can take many forms, and that such forms are within the scope of the invention as claimed. Therefore, the spirit and scope of the appended claims should not be limited to the description of the preferred versions contained herein.

I claim:

1. An apparatus for measuring a hue of a predetermined primary color included in a beam of light reflected from a surface of a bulbus oculi, the apparatus having:
    a diffuse light source for creating a beam of incident light comprising a plurality of primary colors including the predetermined primary color, the beam of incident light being directed onto the surface, the beam of incident light being substantially coaxial with an incident light beam axis;
    the beam of incident light being reflected from the surface to produce the beam of reflected light, the beam of reflected light being substantially coaxial with a reflected light beam axis;
    a photometer positioned for receiving and analyzing said reflected light to provide objective chromaticity data representing the hue of the predetermined primary color;
    a support for positioning the surface in a predetermined position relative to the light source and the photometer, and further additionally including at least one target for viewing by the patient to position the surface in the predetermined position relative to the light source and the photometer;
    the incident light beam axis and the reflected light beam axis forming a predetermined angle between approximately 30° and approximately 50°; and
    a scale adapted for converting said objective chromaticity data to a clinical score measuring the hue of the predetermined primary color in said reflected light,
    whereby, when said incident light is directed onto the surface and the incident light beam axis and the reflected light beam axis form the predetermined angle, reflected light is received and analyzed by the photometer to provide said objective chromaticity data, and the scale converts said objective chromaticity data to the clinical score to measure the hue of the predetermined color in said reflected light.

2. An apparatus according to claim 1 in which the predetermined angle is approximately 45°.

3. An apparatus according to claim 1 in which the predetermined primary color is red.

4. An apparatus for measuring a hue of a predetermined primary color included in a beam of light reflected from a surface of a tarsal area of an eyelid, the apparatus having:
    a diffuse light source for creating a beam of incident light comprising a plurality of primary colors including the predetermined primary color, the beam of incident light being directed onto the surface of the body part, the beam of incident light being substantially coaxial with an incident light beam axis;
    the beam of incident light being reflected from the surface of the body part to produce the beam of reflected light, the beam of reflected light being substantially coaxial with a reflected light beam axis;
    a photometer for receiving and analyzing reflected light to provide objective chromaticity data representing the hue of the predetermined primary color;
    a support for positioning the surface in a predetermined position relative to the light source and the photometer;
    at least one target for viewing by the patient to position the surface in a predetermined position relative to the light source and the photometer;
    the incident light beam axis and the reflected light beam axis forming a predetermined angle between approximately 30° and approximately 50°; and
    a scale adapted for converting said objective chromaticity data to a clinical score measuring the hue of the predetermined primary color in said reflected light,
    whereby, when said incident light is directed onto the surface and the incident light beam axis and the reflected light beam axis form the predetermined angle, reflected light is received and analyzed by the photometer to provide said objective chromaticity data, and the scale converts said objective chromaticity data to the clinical score to measure the hue of the predetermined color in said reflected light.

5. A method of measuring a hue of a predetermined primary color included in light reflected from a surface of a bulbus oculi of a subject, the method comprising the steps of:
   (a) providing a diffuse light source for creating a beam of incident light comprising a plurality of primary colors including the predetermined primary color, the beam of incident light being directed onto the surface, the beam of incident light being substantially coaxial with an incident light beam axis, the beam of incident light being reflected from the surface to produce a beam of reflected light, the beam of reflected light being substantially coaxial with a reflected light beam axis;
   (b) providing a photometer for receiving and analyzing said reflected light to provide objective chromaticity data representing the hue of the predetermined primary color;
   (c) providing a support for the subject's head and at least one target for viewing by the subject, to position the surface in a predetermined position relative to the light source and the photometer such that said reflected light is directed to the photometer;
   (d) positioning the light source and the photometer relative to each other and to the surface such that the incident light beam axis and the reflected light beam axis form an angle of between approximately 30° and approximately 50°; and
   (e) providing a scale adapted for converting said objective chromaticity data to a clinical score measuring the hue of the predetermined primary color in said reflected light.

6. A method of measuring a hue of a predetermined primary color included in a beam of light reflected from a surface of a tarsal area of a subject's eyelid, the method comprising the steps of:
   (a) providing a diffuse light source for creating a beam of incident light comprising a plurality of primary colors including the predetermined primary color, the beam of incident light being directed onto the surface, the beam of incident light being substantially coaxial with an incident light beam axis, the beam of incident light being reflected from the surface to produce the beam of reflected light, the beam of reflected light being substantially coaxial with a reflected light beam axis;
   (b) providing a photometer for receiving and analyzing the reflected light to provide objective chromaticity data representing the hue of the predetermined primary color;
   (c) providing a support for the subject's head and at least one target for viewing by the subject, to position the surface in a predetermined position relative to the light source and the photometer such that the incident light beam axis and the reflected light beam axis form an angle of between approximately 30° and approximately 50°; and
   (d) providing a scale adapted for converting said objective chromaticity data to a clinical score measuring the hue of the predetermined primary color in said reflected light.

7. A method according to claim 6 in which the angle between the incident light beam axis and the reflected light beam axis is approximately 45°.

8. A method of assessing a condition of a bulbus oculi of a subject by measuring redness included in light reflected from a surface of an exposed portion of the bulbus oculi, the method comprising the steps of:
   (a) providing a diffuse light source for creating a beam of incident light comprising a plurality of primary colors including red directed onto the exposed portion of the bulbus oculi, the beam of incident light being substantially coaxial with an incident light beam axis, the beam of incident light being reflected from the surface to produce a beam of reflected light, the beam of reflected light being substantially coaxial with a reflected light beam axis;
   (b) providing a photometer for receiving and analyzing said reflected light to provide objective chromaticity data representing redness in the reflected light;
   (c) providing a support for the subject's head and at least one target for viewing by the subject, to position the surface in a predetermined position relative to the light source and the photometer such that said reflected light is directed to the photometer;
   (d) positioning the light source and the photometer relative to each other and to the surface such that the incident light beam axis and the reflected light beam axis form an angle of between approximately 30° and approximately 50°;
   (e) providing a scale adapted for converting said objective chromaticity data to a clinical score measuring redness in said reflected light; and
   (f) comparing the clinical score to a control clinical score measuring a control hue of red related to a predetermined health condition of the bulbus oculi;
   whereby the condition of the bulbus oculi is assessed.

9. A method of assessing a condition of a tarsal area of an eyelid of a subject by measuring redness included in light reflected from a surface of an exposed portion of the tarsal area, the method comprising the steps of:
   (a) providing a diffuse light source for creating a beam of incident light comprising a plurality of primary colors including red directed onto the exposed portion of the tarsal area, the beam of incident light being substantially coaxial with an incident light beam axis, the beam of incident light being reflected from the surface to produce a beam of reflected light, the beam of reflected light being substantially coaxial with a reflected light beam axis;
   (b) providing a photometer for receiving and analyzing said reflected light to provide objective chromaticity data representing redness in the reflected light;
   (c) providing a support for the subject's head and at least one target for viewing by the subject, to position the surface in a predetermined position relative to the light source and the photometer such that said reflected light is directed to the photometer;
   (d) positioning the light source and the photometer relative to each other and to the surface such that the incident light beam axis and the reflected light beam axis form an angle of between approximately 30° and approximately 50°;
   (e) providing a scale adapted for converting said objective chromaticity data to a clinical score measuring redness in said reflected light; and
   (f) comparing the clinical score to a control clinical score measuring a control hue of red related to a predetermined health condition of the tarsal area;
   whereby the condition of the tarsal area is assessed.

* * * * *